United States Patent
Vollweiler et al.

[11] Patent Number: 5,854,432
[45] Date of Patent: Dec. 29, 1998

[54] DUAL TUBE SAMPLING SYSTEM

[76] Inventors: Arthur R. Vollweiler; Timothy J. Vollweiler, both of 105 Harrison, American Falls, Id. 83211

[21] Appl. No.: 969,752

[22] Filed: Nov. 13, 1997

[51] Int. Cl.⁶ ........................................................ G01N 1/04
[52] U.S. Cl. .......................................................... 73/864.44
[58] Field of Search ........................... 73/864.44, 864.45; 175/403, 405, 20

[56] References Cited

U.S. PATENT DOCUMENTS

| | | | |
|---|---|---|---|
| 1,109,446 | 9/1914 | Melberg | 175/405 |
| 3,447,615 | 6/1969 | Schick | 73/864.44 |
| 5,488,876 | 2/1996 | Casey et al. | 73/864.45 |
| 5,606,139 | 2/1997 | Wittig et al. | 73/864.44 |

FOREIGN PATENT DOCUMENTS

| | | | |
|---|---|---|---|
| 4020207 | 1/1992 | Germany | 73/864.44 |

Primary Examiner—Robert Raevis
Attorney, Agent, or Firm—K. S. Cornaby

[57] ABSTRACT

The invention pertains to the art of direct push soil sampling that uses the art of dual tube to retrieve subsurface soil samples. It is a means of applying the dual tube art that allows deeper sampling depths to be achieved by configuring the tooling string in such a manner that the inner tooling is non-rigidly attached to the outer tooling string both rotationally and axially. The non-rigidity of integration of the two tooling strings allows deeper penetration of the sampling apparatus by reducing the friction between soil entering the sample chamber of the inner tooling string and the sample chamber. In addition deeper depths of penetration are possible because the inner and outer tooling strings are driven both concurrently and independently of each other.

6 Claims, 3 Drawing Sheets

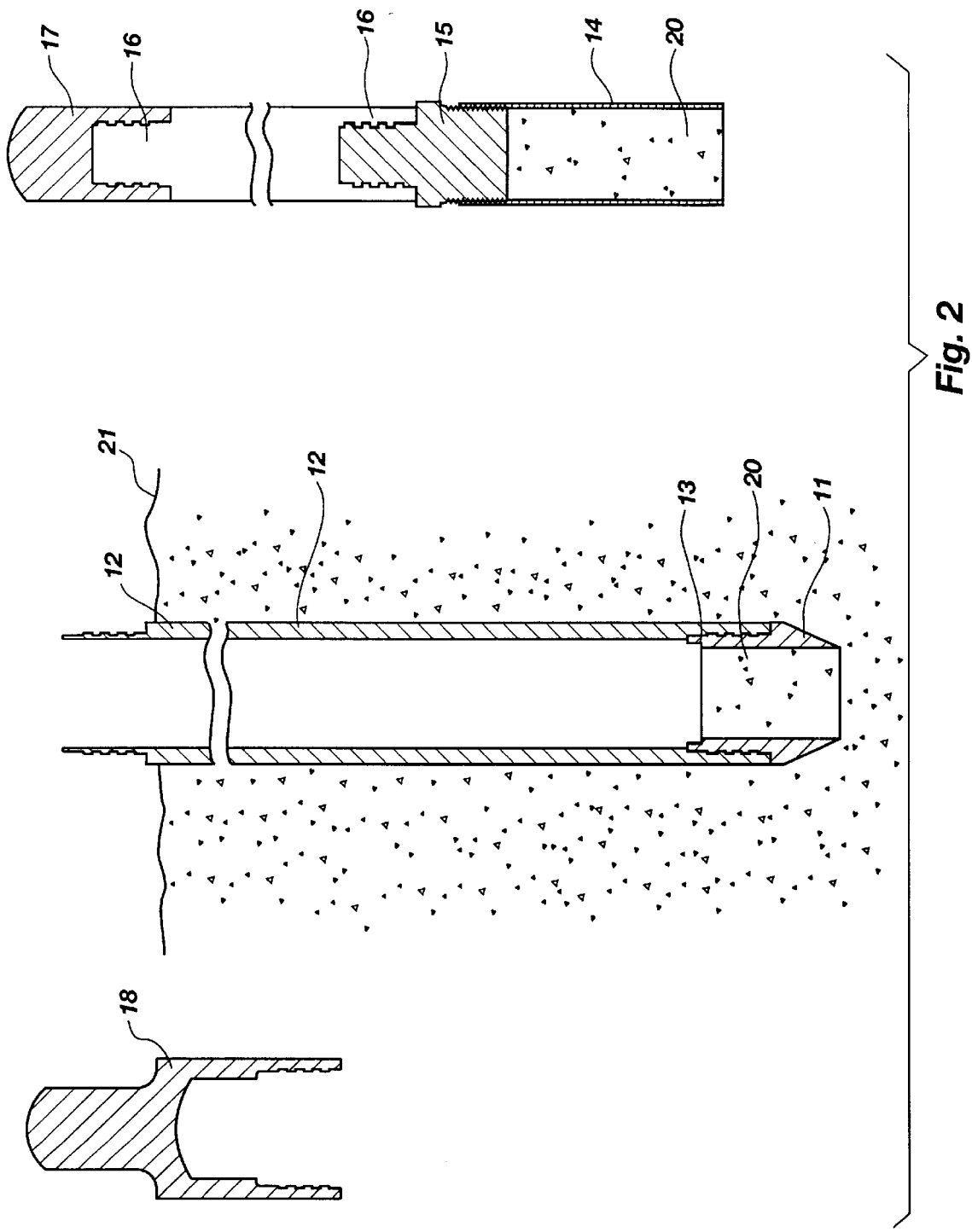

DUAL TUBE SAMPLING SYSTEM

BACKGROUND OF THE INVENTION

In the past and currently societies have been and are required to probe the earth's subsurface to get information in order to answer questions pertaining to such things as mineral content, construction requirements and environmental concerns to name a few. Because of the needs and desires for subsurface information, different technologies have evolved for the exploration of which direct push technology is one.

The basic direct push technology is a method of exploration which uses a hammering or impacting device to drive a conical point into the ground using cylindrical rods, that are sometimes hollow, to depths ranging from zero feet to in excess of one-hundred feet. Many organizations either use direct push technology for exploration or market the technology.

Direct push technology is used to collect different kinds of subsurface data in the form of soil samples. Consequently specialized techniques have been developed for specific sampling needs. Because of the specialized techniques, modifications to the basic direct push technology have resulted along with the development of new specialized tooling. Tooling refers to any of the apparatuses or mechanisms that are used in direct push technology to obtain data or samples.

One of the developments is a method that is known as a dual tube system. The dual tube system was adapted from auguring or well drilling technology where hollow flyted augers are used with a drill bit that has a removable center. The removable center allows for different tasks to be performed through the bottom of the bore hole using apparatuses attached to extensions that are lowered through the center of the flytes. In a dual tube system the conical point has been made into two separate pieces, the inner point and the outer point or drive shoe. The two pieces are made to work as a unit performing the same function as the conical point in basic direct push technology; however, the inner point can be removed to perform tasks required during sampling operations. The dual tube system uses the cylindrical rod to force the drive shoe into the ground; but a means of holding the inner point in position relative to the drive shoe is required since it is not rigidly attached to the drive shoe. The means is another cylindrical rod that will fit down through the interior of the original rod that is attached to the drive shoe. There are now two rods, the outer rod and the inner rod. Because there are two rods used with direct push technology that use the dual tube system, adapters have been made that allow both the inner point and the drive shoe to be driven concurrently. Adapters rigidly couple the inner and outer rods. By adding extensions to both the outer and inner drive cylinders, the drive shoe and inner point can be driven to great depths. At any point along the way, the inner point can be removed to perform some sampling task and then reinserted so that the tooling can be driven deeper into the ground.

The dual tube system has been a major advancement in direct push technology and has allowed for the development of some highly informative types of samples. One type is called a continuous core sample. From a continuous core sample a soil profile can be made. A soil profile is comprised of data from a column of soil that may start from the surface and be continuous to a depth of twenty, forty, fifty feet or more.

Two methods are used to retrieve a continuous core sample. One method starts out by driving a sample chamber that will fit through the center of the drive shoe into the earth. It is removed and the sample is identified and stored. The drive shoe with center point and one set of outer and inner extensions are then driven into the hole that was left by the sample chamber. When the drive shoe and inner point reach the bottom of the hole, the center point and inner rod are then removed and an empty sample chamber is then inserted inside of the outer rod down to the depth of the drive shoe. The sample chamber is then driven through the drive shoe until it has been filled with soil. The sample chamber with soil inside is removed from the hole and the sample is identified and stored. The inner point along with the inner rod is inserted back inside of the outer rod and lowered until the inner point is protruding from the bottom of the drive shoe. A set of outer and inner rods or extensions are attached and a drive adaptor is connected to them so that the entire collection of tooling, now called a string, can be driven farther into the ground. The string is driven until the drive shoe and inner point are once again at the bottom of the hole left by the sample chamber. The process just described is repeated until the desired depth of the soil profile has been reached. This method has one major drawback in that soil is scraped off of the sides of the hole left by the sample chamber and deposited on the bottom of the hole as the drive shoe is being driven to the next sampling depth interval. When the sample chamber collects the soil for the depth interval, it is also retrieving soil from the previous depth interval which means that the condition of cross contamination has occurred, an undesirable condition. A second drawback to this method of continuous coring is that a large amount of time is consumed coupling and uncoupling the inner rods when inserting and removing the inner point and sample chamber.

The second method for retrieving a continuous core sample using the dual tube system eliminates the use of the inner point and drives the drive shoe, the sample chamber which will not fit through the drive shoe, and the outer and inner extensions in unison. Using the second method, the drive shoe is attached to an outer rod and the sample chamber is inserted inside of the outer rod until its lower opening is in contact with the drive shoe. A drive adaptor is attached to the outer rod and the assembly is driven into the earth until the sample chamber is full of soil, at which time the drive adaptor is removed from the outer rod and the sample chamber is removed from the interior of the outer rod. The sample is identified and stored. A sample chamber is reinserted inside of the outer rod and an inner rod is attached to its top end. An outer rod extension is attached to the top of the outer rod that has already been driven into the ground. A hammer adaptor that tie the inner and outer rods together is attached to the top end of the outer and inner rods. The entire assembly is then driven further into the earth until the sample chamber is full of soil. The hammer adaptor is then removed and the sample chamber is pulled from the string of outer rods using the inner rod. The sample is identified and stored. A sample chamber is attached to the inner rod and an additional inner rod is attached to the upper end of the inner rod attached to the sample chamber. The sample chamber and inner rods are reinserted into the outer rods, the hammer adaptor attached and the assembly is driven further into the earth until the sample chamber is full. The sampling process is continued until the desired depth of the soil profile is completed.

The second method of continuous coring eliminates the cross contamination that plagues the first method and reduces the time required to collect a column of soil since the use of the inner point is eliminated, thus eliminating fifty percent of the number of connections and disconnections of the inner rods during a continuous core collection. The art used in the second method of direct push technology was demonstrated as early as 1939 by F. C. Sturges (U.S. Pat. No. 2,165,685) with numerous applications since in other patents, the latest known one being in 1996 by Michael B. Casey and Murry D. Einarison (U.S. Pat. No. 5,488,876).

The art of dual tubing sampling can be improved upon, however, by replacing the rigid sample chamber with a chamber that possess a modulus of elasticity which is substantially less than that of the rest of the dual tube tooling. In addition greater depths can be achieved if the sample chamber is allowed to move relative to the outer drive casing and drive shoe both axially and rotationally.

SUMMARY OF THE INVENTION

As described in the section, Background of The Invention, typical dual tube sampling systems are comprised of the following components: an impacting device such as a hydraulic hammer, a drive adaptor that transfers the force of the impacting device to a set of inner and outer drive rods while protecting the threads of the uppermost outer drive rod, a thread protector or adaptor is also used to protect the threads of the uppermost inner drive rod, a coupler that connects the lower end of the lowermost inner rod to a sample chamber, a drive shoe that is attached to the lower end of the lowermost outer drive rod, and usually a center plug or point for the drive shoe.

The improvements to dual tube sampling about to be described use the techniques described in method two in Background of the Invention with two deviations which enhance the art of dual tube sampling. First, the sample chamber is in no way attached rigidly to any part of the outer casings or drive shoe. Motion of the sample chamber is allowed both rotationally and axially relative to the outer tooling assembly. However, the sample chamber is rigidly coupled to the inner tooling string which is allowed to move both rotationally and axially relative to the outer tooling. Axial motion is further allowed by constructing the inner and outer tooling so that when assembled with the sample chamber inside the outer rod assembly the length of the inner assembly is less than the length of the outer assembly. Secondly, the sample chamber is made of a material that is substantially less rigid than the rest of the tooling making up the dual tube system. In addition the elasticity of the sample chamber is much greater than the rest of the tooling used in the system.

The modifications mentioned are desired because axial motion will allow the inner and outer assemblies to be driven both independently and concurrently. Increased elasticity of the sample chamber relative to the rest of the tooling allows the diameter of the sample chamber to fluctuate as it is being driven down around a soil sample. Fluctuation in sample chamber diameter is desirable because friction between the sample chamber walls and the aggregate in the soil is reduced as the diameter of the sample chamber is increased.

The inner and outer tooling assemblies can be driven both independently and concurrently because, if the outer drive casing assembly is longer than the inner assembly, two situations can occur at the moment of impact by the driving device. In one situation, the upper end of the inner drive assembly will be in direct contact with the hammer drive adaptor attached to the upper end of the outer drive assembly. When the contact is present, the impact of the hammer will be transferred through the drive adaptor directly to the inner string of tooling. The inner string of tooling will be advanced before the outer string of tooling and no advancement of the outer string will occur until the bottom end of the inner string makes contact with the bottom end of the outer string. On the other hand, if the upper end of the inner string is not in contact with the upper end of the outer string, no energy is transferred to the inner tooling until the outer tooling has advanced enough to make up the difference in length of the two tool strings. Therefore, if the impacting device has an impacting frequency of two-hundred beats per minute, then theoretically fifty percent of the impact loads are initially transferred to the inner string and the other fifty percent is transferred directly to the outer string of tooling. Since the inner and outer tooling assemblies are driven independently of each other, total over all friction that must be overcome with each blow of the impacting device is reduced and greater depths can be achieved.

Resistance of the soil sample is also reduced by allowing the inner tooling with sample chamber attached to rotate within the outer tooling relative to the outer tooling. Drag of soil particles on both the inner wall of the sample chamber and the outer wall of the outer tooling causes a rotational resistance. Allowing the tooling to rotate as it is being driven reduces the total overall resistance.

As mentioned, dual tube sampling is enhanced by constructing the sample chamber of a material that is substantially higher in elasticity. The condition of increased elasticity is desirable because, when the sample chamber meets resistance on the bottom end, the downward force applied on the top end causes its diameter to increase in size; but, depending on the cohesive nature of the soil being sampled, the diameter of the soil remains the same since no overhead load is being applied to it. Once again the friction of sample retrieval is reduced.

It is obvious that reduced friction will increase the depth that a dual tube sampling system can achieve. It will become apparent that having a dual tube sampling system that allows the sample chamber to move both axially and rotationally relative to the outer rod assembly will cause friction to be reduced. It will also become obvious that insuring that no contact resulting in a rigid coupling between the inner and outer rod assemblies is the only sure means of allowing radial and axial motion.

BRIEF DESCRIPTION OF THE DRAWINGS

FIG. 2 shows the dual tube sampling apparatus after it has been driven to depth and the inner rod assembly removed with a soil sample inside the sample chamber.

DETAILED DESCRIPTION OF THE DRAWINGS

Figure 1:
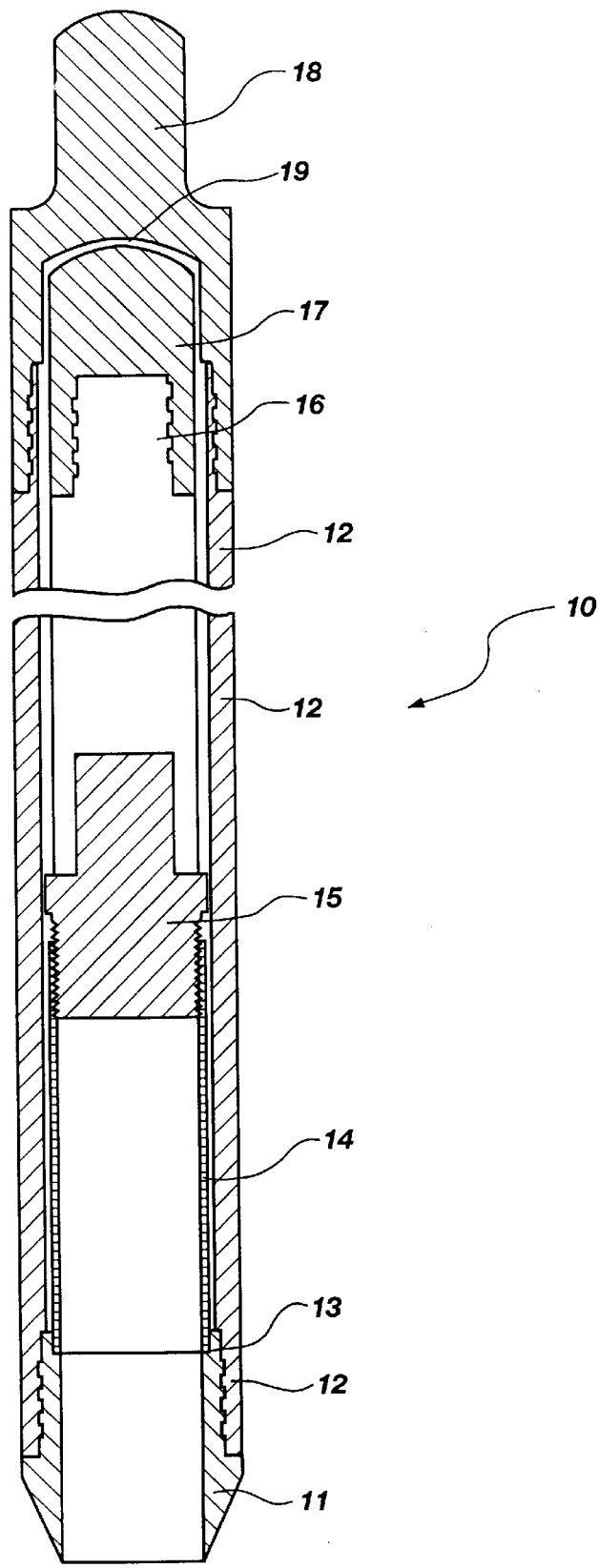
FIG. 1 depicts the preferred embodiment of the dual tube sampling apparatus.

FIG. 1 shows the preferred embodiment of a dual tube sampling system. The lower most part of the system is the drive shoe 11. The drive shoe 11 is typical of most drive shoes used in dual tube direct push technology. It is made from an alloy type steel with its lower exterior edge tapered to deflect soil directly below, outward away from its opening as the sampling apparatus 10 is being driven into the earth. It has a threaded section that is compatible with the threads of the outer rods 12. A lip 13 has been formed into the top interior edge of the drive shoe 11 that the sample chamber 14 can rest on. The drive shoe 11 has an opening that runs clear through it which is typical. The diameter of the opening is normally the same diameter as the inner diameter of the sample chamber 14. Some dual tube systems make the opening in the drive shoe 11 slightly smaller than the inner diameter of the sample chamber 14 to allow soil to enter the sample chamber 14 more freely. The bottom end of the outer rod 12 is shown threaded onto the drive shoe 11. Supported vertically on a lip 13 in the top of the drive shoe 11 is the sample chamber 14. Threaded into the top end of the sample chamber 14 is a coupling 15. The coupling 15 rigidly attaches the sample chamber 14 to the inner drive rods 16. The outer rods 12 and the inner rods 16 are usually made from an alloy that has lower durability than the drive shoe 11. Threaded to the top of the inner rods 16 is a thread protector 17. The thread protector 17 is typical of most dual tube direct push systems and is made of an alloy steel that has the same durability as the inner rods 16. Threaded to the top of the outer rods 12 is the hammer adaptor 18. The hammer adaptor 18 is also typical of most dual tube direct push systems. It also is made of alloy steel that has the same durability as the outer rods 12. Notice that the thread protector 17 is not rigidly attached to the hammer adaptor 18 and that the top interior is concave whereas the top exterior of the thread protector 17 is convex with a smaller radius than the hammer adaptor 18. Also notice that the exterior walls of the thread protector 17 do not come into contact with the interior walls of the hammer adaptor 18. This has been done to allow for some deformation of both the hammer adaptor 18 and the thread protector 17. If allowances for deformation are not made the thread protector 17 will eventually be lodged inside of the hammer adaptor 18 rigidly coupling the inner and outer tooling strings together. Also notice the gap 19 between the inner rod thread protector 17 and the hammer adaptor 18. The gap 19 is provided so that the inner and outer tooling strings are driven independently of each other by the impacting device. The inner tooling is therefor not rigidly attached to the outer tooling of this preferred embodiment of the dual tube direct push sampling apparatus. An impacting device is not shown in FIG. 1 or any of the following figures because it can be any type of device capable of providing an impacting force to the dual tube apparatus 10.

FIG. 2 depicts the dual tube sampling system in use after the inner rod 16 assembly has been removed from the outer rod 12 assembly. The inner and outer tooling strings have been driven into the earth 21 to the point that the sample chamber 14 contains a soil sample 20 and the sampling apparatus 10 removed from the earth 21. The hammer adaptor 18 has been removed from the top of the outer rod assembly 12. The thread protector 17 inner rods 16 and sample chamber 14 containing a soil sample 20 have been removed from the outer rod 12 and drive shoe 11 assembly. Soil will remain in the lower portion of the drive shoe 11 when the sample chamber is removed. The next step in the sampling process is to detach the sample chamber 14 from the coupling 15 and prepare the soil sample 20 for storage, shipping or analysis. A sample chamber 14 can once again be attached to the coupling 15 and another sample from a deeper depth taken.

Figure 3B:
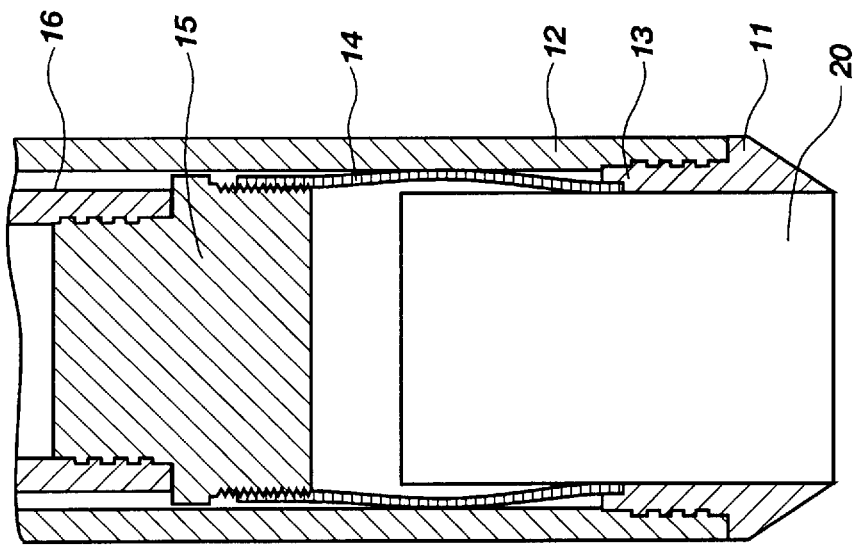
FIGS. 3A and 3B show the deformity of the sample chamber.
Figure 3A:
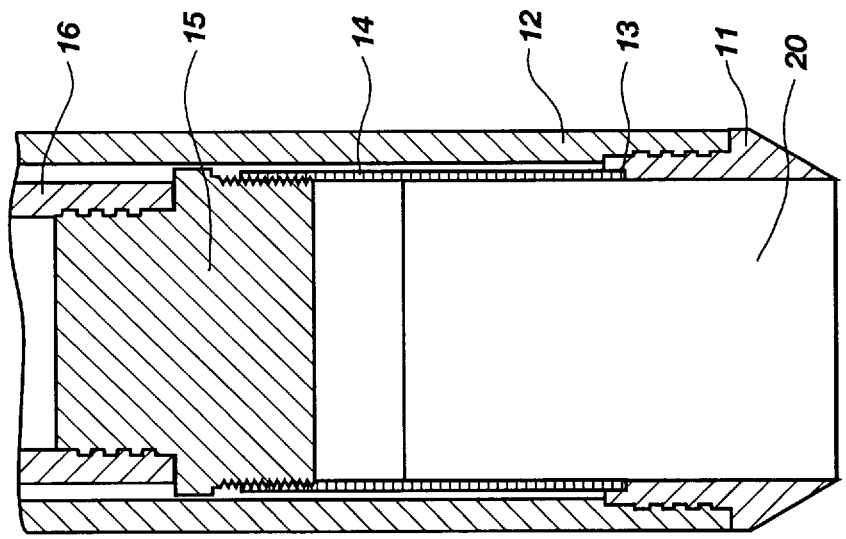

FIGS. 3A and 3B depict the sample chamber 14 in it's natural unstressed state and its deformed stressed state. The sketches have been exaggerated to show the deformity of the sample chamber 14 in FIG. 3B. When an overhead vertical force is applied to the top of the sample chamber 14 by the inner drive rod assembly 16 and the bottom end meets resistance by the shoulder 13 in the top of the drive shoe 11 the elasticity of the material allows its walls to expand radially until they make contact with the inner walls of the lowermost outer rod 12. Since the soil sample 20 experiences no overhead force, the cohesiveness of the soil causes the soil sample 20 to retain it's original geometry while the sample chamber 14 is deformed. When the overhead force from the inner rods 16 is removed, the sample chamber 14 returns to its natural unstressed state. It is apparent that, due to the lack of contact between the inner walls of the sample chamber 14 and the soil sample 20 during the deformed stressed state of the sample chamber 14 friction is reduced.

While this invention has been described and illustrated herein with respect to preferred embodiments, it is understood that alternative embodiments and substantial equivalents are included within the scope of the invention as defined by the appended claims.

What is claimed:

1. A dual tube sampling apparatus for subsurface material exploration, comprising in combination:
   an outer hollow drive tube having a respective upper and a lower end;
   a hollow drive shoe attached to the lower end of the outer hollow drive tube, said drive shoe adapted to contact material to be sampled;
   an inner drive tube having a respective upper and lower end; said inner drive tube being disposed unattached and concentrically within the outer hollow drive tube;
   a hollow sample chamber connected to the lower end of the inner drive tube disposed at least partially within the drive shoe; said sample chamber having a modulus of elasticity substantially less than the outer driving tube; and
   means for transferring vertical impact to both inner and outer driving tubes.

2. An apparatus as set forth in claim 1, wherein said sample chamber is nonrigidly connected to any part of the outer drive tube.

3. An apparatus as set forth in claim 1, wherein said sample chamber expands in diameter as vertical load is applied and returns to its original shape when compressive load is removed.

4. An apparatus as set forth in claim 1, wherein said inner drive tube and said outer drive tube are capable of being moved both independently and concurrently with respect to each other.

5. An apparatus as set forth in claim 1, wherein said outer drive tube supports a semi-rigid sample chamber when compressive loads are applied.

6. An apparatus as set forth in claim 1, wherein at least one additional outer drive tube is attached end-to-end with the upper end of said outer drive tube, and at least one additional inner drive tube is attached end-to-end with the upper end of said inner drive tube.

* * * * *